(12) United States Patent
Bryson, Jr. et al.

(10) Patent No.: US 6,249,919 B1
(45) Date of Patent: Jun. 26, 2001

(54) PASSIVE DEODORIZATION DEVICE

(75) Inventors: John D. Bryson, Jr., Brookfield; George P. Roberts, Racine, both of WI (US); Wolfgang Clemens, Wachtberg/Liesseh; Stephan Dupont, Andernach, both of (DE); Joseph J. Hennessey, Howards Grove; David L. Vergara, Oconomowoc, both of WI (US)

(73) Assignee: Vaportex, Inc., Sussex, WI (US)

( * ) Notice: Subject to any disclaimer, the term of this patent is extended or adjusted under 35 U.S.C. 154(b) by 0 days.

(21) Appl. No.: 09/244,926

(22) Filed: Feb. 4, 1999

(51) Int. Cl.[7] ........................................ E03D 9/04
(52) U.S. Cl. ........................... 4/209 R; 4/449; 4/462; 422/123
(58) Field of Search ........................ 4/209 R, 222, 4/229, 228.1, 462, 463, 475, 477, 449; 424/76.7; D23/366, 368, 369; 422/123, 124

(56) References Cited

U.S. PATENT DOCUMENTS

| | | | |
|---|---|---|---|
| 1,963,501 | * 6/1934 | Mitchell | 4/222 |
| 2,545,755 | * 3/1951 | Ward | 4/209 R |
| 3,538,866 | * 11/1970 | Gaines | 422/123 |
| 3,747,902 | * 7/1973 | Bailey | 4/209 R |
| 3,902,877 | * 9/1975 | Swaim | 422/123 |
| 5,086,523 | * 2/1992 | DeMott et al. | 4/229 |
| 5,820,792 | * 10/1998 | Lin | 422/124 |
| 6,103,201 | * 8/2000 | Green | 422/124 |

FOREIGN PATENT DOCUMENTS

4009162 * 11/1990 (DE) ........................................ 4/228

* cited by examiner

Primary Examiner—Charles R. Eloshway
(74) Attorney, Agent, or Firm—Quarles & Brady LLP

(57) ABSTRACT

The present invention provides a passive deodorization device suitable for use in a portable toilet enclosure having a vent tube for venting odors from a holding tank. The deodorization device has a housing having an engagement surface for engaging a vent tube outer surface, and an aperture. Two fingers extend from the aperture into the vent tube. A retention member mounted on the fingers engage a vent tube inner surface and clamp the vent tube wall between the housing and retention member. A deodorizing element slipped into the aperture between the fingers deodorizes the malodorous vapors associated with the toilet.

4 Claims, 4 Drawing Sheets

US 6,249,919 B1

PASSIVE DEODORIZATION DEVICE

TECHNICAL FIELD

The present invention relates to a deodorization device, and more particularly to a passive deodorization device suitable for use with a portable toilet having a vent tube extending from a holding tank.

BACKGROUND OF THE INVENTION

Portable toilets in self standing enclosures or found in the transportation industry have a seating area disposed above a holding tank. A vent tube extends from the holding tank to vent the holding tank to the atmosphere. This vent tube often passes through the enclosure to vent the holding tank through the enclosure top. Malodorous vapors emanating from the holding tank foul the air in and around the enclosure.

One method of masking the odor inside the enclosure includes mounting an air freshener, which releases a pleasant aroma, to an interior enclosure wall. This particular method does not solve the odor problem outside of the enclosure. Furthermore, after an extended period of time inside the enclosure, the spent air freshener must be manually replaced. A users hands may become soiled when removing the spent air freshener assembly or exchanging the spent air freshener element inside a housing. Furthermore, the air freshener may be removed prematurely by an enclosure visitor, subjecting subsequent visitors to the malodorous vapors associated with the toilet.

SUMMARY OF THE INVENTION

The present invention provides a passive deodorization device suitable for use in a portable toilet enclosure having a vent tube for venting odors from a holding tank. The deodorization device has a housing with an engagement surface for engaging a vent tube outer surface, and an aperture. Two fingers extend from the aperture into the vent tube. A retention member mounted on the fingers engage a vent tube inner surface and clamps the vent tube wall between the housing and retention member. A deodorizing element slipped into the aperture between the fingers deodorizes the malodorous vapors associated with the toilet.

A general objective of the present invention is to provide a deodorization device capable of treating malodorous vapors inside an enclosure and exiting a holding tank vent tube. This objective is accomplished by providing a device which is inserted into the vent tube through a hole formed therein which passes through the enclosure. This allows mounting the device in the vent tube from inside the enclosure exposing the deodorizing element to the air inside the enclosure and the vent tube.

Another objective of the present invention is to prevent the easy removal of the deodorization device once installed. This accomplished by providing retention members which are self-locking and, thus, prevent device removal from the vent tube.

Still another objective of the present invention is to provide a method for easy replacement and disposal of a spent deodorizing element. This objective is accomplished by providing a housing having an aperture, and fingers extending therefrom to hold a deodorizing element. The spent element is replaced by inserting the replacement deodorizing element into the aperture; forcing the spent deodorizing element out of the grasp of the fingers, and allowing the spent deodorizing element to fall through the vent tube into the holding tank.

The foregoing and other objects and advantages of the invention will appear from the following description. In the description, reference is made to the accompanying drawings which form a part hereof, and in which there is shown by way of illustration a preferred embodiment of the invention.

DETAILED DESCRIPTION

Figure 1:
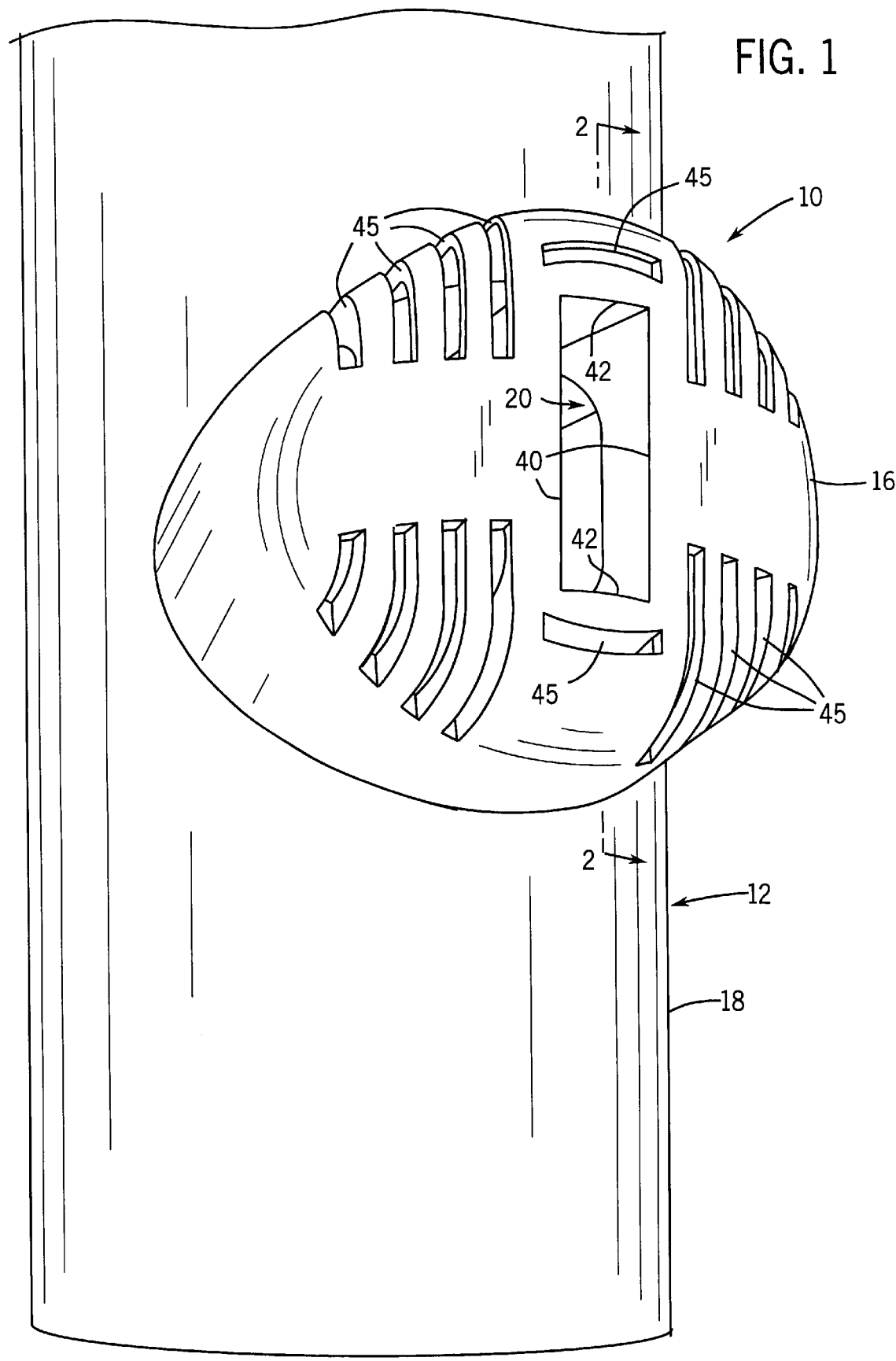
FIG. 1 is a perspective view of deodorization device incorporating the present invention installed in a vent tube.
Figure 2:
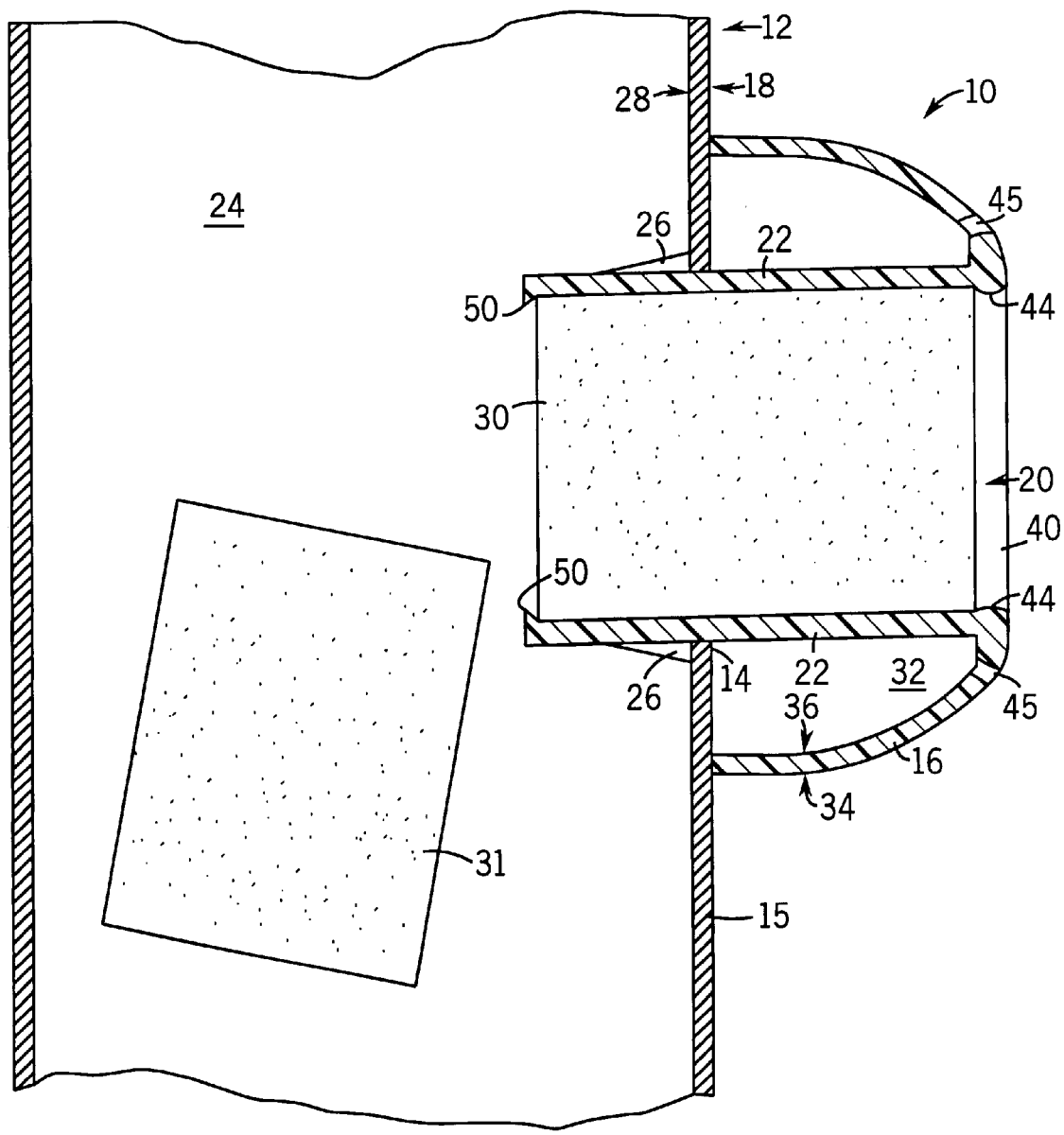
FIG. 2 is a schematic cross sectional view of the deodorization device and vent tube along line 2—2 of FIG. 1.

As shown in FIGS. 1 and 2, a passive deodorization device 10 attaches to a vent tube 12 for a portable toilet compartment. The vent tube 12 extends from a holding tank (not shown) disposed beneath a seating area of the toilet compartment through the toilet compartment interior and exhausts to the outside. Malodorous fumes originating in the holding tank flow through the vent tube 12 and exhaust into the atmosphere. The passive deodorization device 10 snaps into an opening 14 bored in a wall 15 of the vent tube 12 to treat the malodorous vapors associated with the portable toilet in the vent tube 12 and toilet compartment.

The passive deodorization device 10 has a housing 16 with an aperture 20 formed therein, and fingers 22 extending from the aperture 20 for holding a deodorizing element 30. The housing 16 engages an outer surface 18 of the vent tube 12 with the fingers 22 extending through the vent tube opening 14 in the vent tube interior 24. The fingers 22 have self-locking members 26 which engage a vent tube inner surface 28 and cooperatively clamp onto the vent tube wall 15 with the housing 16 to secure the deodorization device 10 in place. A deodorizing element 30 slipped into the housing aperture 20 is grasped by the fingers 22, and contains agents to neutralize malodorous vapors associated with the portable toilet. Preferably, the deodorization device 10 is formed from molded plastic, such as polyethylene.

Figure 3:
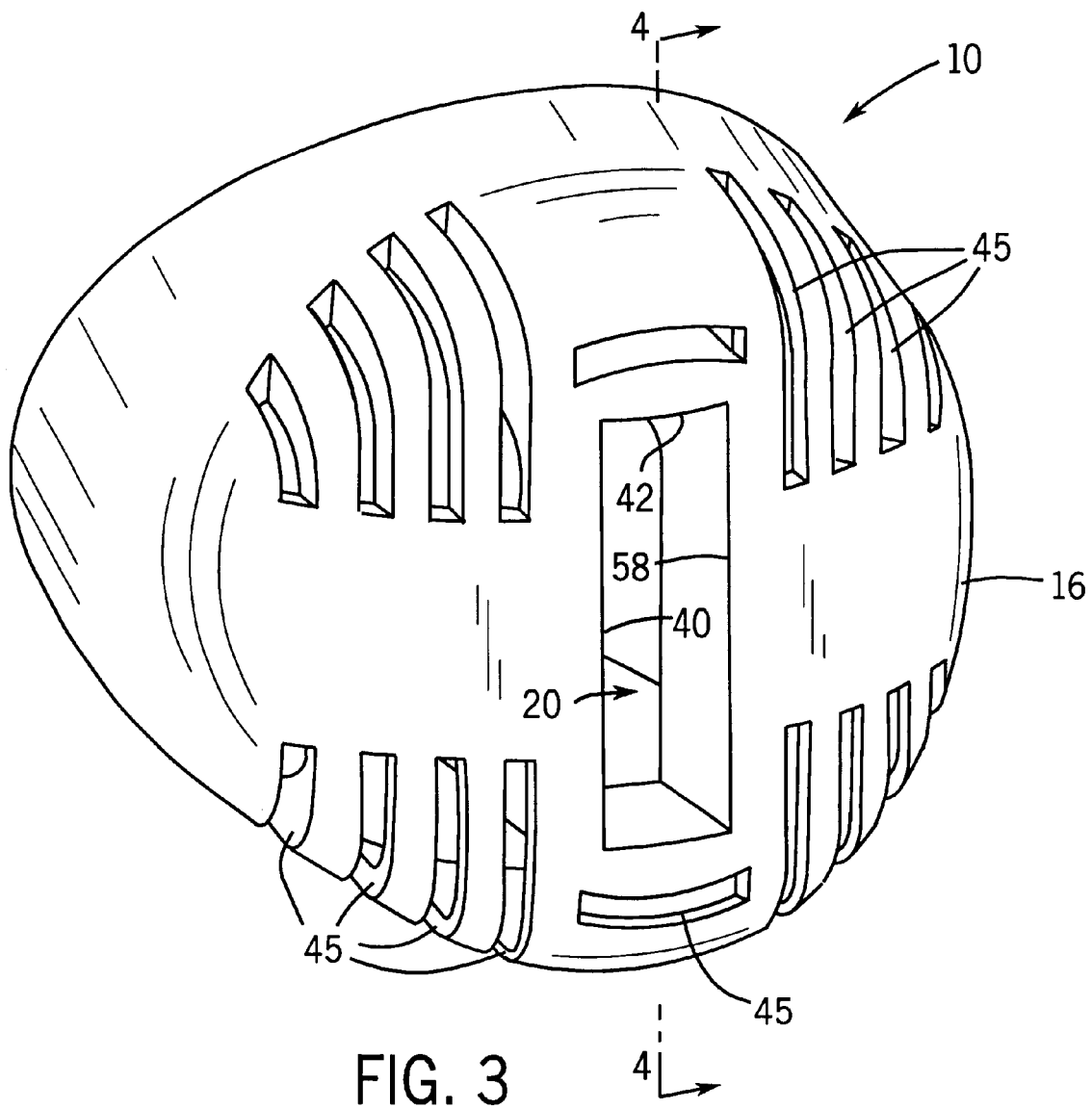
FIG. 3 is a perspective view of the deodorization device of FIG. 1.
Figure 4:
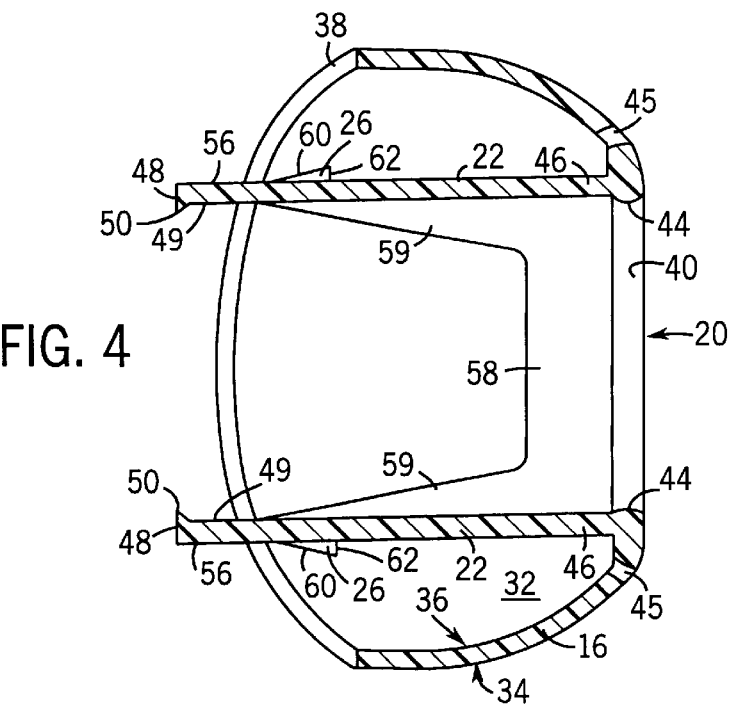
FIG. 4 is a schematic cross sectional view of the deodorization device along line 4—4 of FIG. 3.
Figure 5:
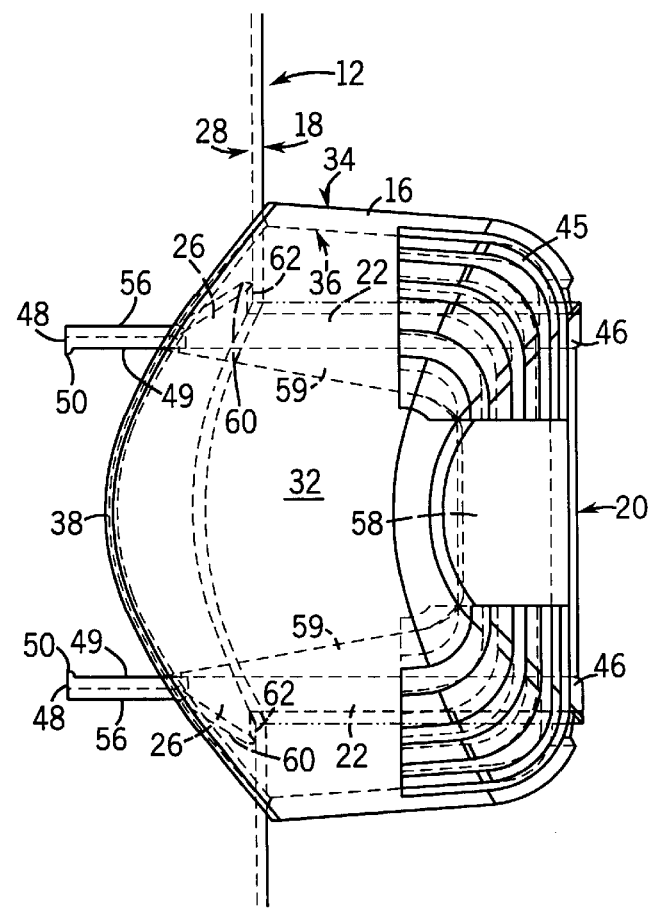
FIG. 5 is a side view of the deodorization device of FIG. 1.

Looking particularly at FIGS. 3–5, the cup shaped housing 16 defines a cavity 32 and has an exterior convex surface 34 and an interior concave surface 36 joined together by an edge 38. The housing edge 38 conforms to and abuts the vent tube outer surface 18 to cooperate with the self-locking members 26 and hold the housing 16 in place. A substantially rectangular aperture 20 formed in the housing 16 has opposing long sides 40 joined by opposing short sides 42, and is sized to receive the generally rectangular deodorizing element 30. A lip 44 formed on the aperture sides 40, 42 extends toward the aperture center to inhibit removal of the deodorizing element 30 through the housing 16. Vents 45 formed in the housing 16 expose the deodorizing element 30 in the housing 16 to air inside the toilet compartment interior. Although a rectangular aperture 20 is shown and described, any shape aperture may be used, such as a round, square, polygonal or the like, depending upon the shape of the deodorizing element 30.

The pair of opposing fingers 22 cooperatively retain the deodorizing element 30 and expose it to the malodorous vapors associated with the portable toilet. Each finger 22 has a proximal end 46 formed as an integral part of the housing 16 and extends from the housing aperture short sides 42 through the cavity 32 toward a finger distal end 48 disposed in the vent tube 12. Each finger 22 has an interior side 49 which engages an opposing side of the deodorizing element 30 to cooperatively grasp the element 30. Ribs (not shown) may be formed along the length of the interior finger side 49 of one or more fingers 22 to improve the grasp on the deodorizing element 30.

Inwardly extending stops 50 formed on the finger distal end 48 interior side 49 inhibit the deodorizing element 30 from being pushed too far through the housing aperture 20 and into the holding tank at the bottom of the vent tube 12. An exterior side 56 of each finger 22 has a self-locking member 26 formed thereon to engage the vent tube inner surface 24. Although two fingers of equal width are shown and described, one finger may be wider than the other to provide protection for the deodorizing element from the elements, such as rain, which may enter the vent tube.

A pair of opposing walls 58 join the finger proximal ends 46 to form a shaft extending generally perpendicularly from the housing aperture 20 into the cavity 32. The shaft walls 58 guide the deodorizing element 30 between fingers 22 extending into the vent tube 12. Preferably, the walls 58 have a tapered portion 59 extending toward the finger distal ends to guide the deodorizing element along the length of the fingers 22. Although the shaft is shown and described as having a smooth interior surface, ridges (not shown) may be formed on the shaft walls 58 to engage the deodorizing element 30 and prevent it from inadvertently slipping out of the fingers 22 and down into the holding tank. Vents (not shown) may also be formed in the walls 58 to increase the exposure of the element 30 to the air inside the cavity 32.

The self-locking members 26 are formed as an integral part of each finger exterior side 56 and engage the vent tube inner surface 28. Each self-locking member 26 has a ramped surface 60 which causes the fingers 22 to deflect inward when passing through the vent tube opening 14, and a locking surface 62 which engages the vent tube inner surface 28 when the ramped surface 60 has passed through the vent tube opening 14. The ramped surface 60 has an increasing depth as it extends away from the finger distal end 48 to deflect the finger 22 inward. The locking surface 62 is substantially parallel to the vent tube inner surface 28 and is formed at the end of the ramped surface 60 having the greatest depth.

Referring to FIGS. 2, 4, and 5, the self-locking member locking surface 62 cooperates with the housing edge 38 to clamp the vent tube wall 15 therebetween and hold the deodorization device 10 in place. Advantageously, the self-locking member 26 prevents easy removal of the deodorization device 10 from the vent tube 12. However, other retention members for securing the device 10 to the vent tube 12 may be used without departing from the scope of the present invention. For example, ribs formed as part of the finger exterior side 56 to providing a friction fit may be used when the vent tube wall thickness is not known, without departing from the scope of the present invention. Other retention members, such as screws, bolts, adhesives, or the like may also be used to mount the deodorization device 10 to the vent tube 12 without departing from the scope of the present invention.

The deodorizing element 30 is an article composed of materials impregnated with agents known in the art. Preferably, the element 30 is biodegradable, such as recycled textiles and paper held together by a binder. The materials are formed into a brick shape having a cross section which slips through the housing aperture 20, and then impregnated with the deodorizing agents, such as natural aromatic oils to mask or neutralize the malodorous vapors associated with the toilet.

Looking back at FIG. 2, the deodorization device 10 is installed by boring an opening 14 having a diameter approximately equal to the distance between the finger exterior sides 22, into the vent tube wall 15. The fingers 22 are then inserted into the vent tube 12 through the opening 14. As the fingers 22 pass through the vent tube opening 14, the self-locking member ramped surfaces 60 formed on the finger exterior side 56 cause the fingers 22 to deflect inward. Once the ramped surfaces 60 pass through the vent tube opening 14, the fingers 22 spring outward causing the locking surfaces 62 to engage the vent tube inner surface 28 and clamp the vent tube wall 15 between the locking surfaces 62 and the housing edge 38, thus locking the deodorization device 10 in place. Preferably, the deodorization device 10 is oriented such that the fingers 22 are vertically aligned in the vent tube 12 allowing the lower finger 22 to support the deodorizing element 30.

The deodorizing element 30 is inserted into the housing aperture 20 to complete the assembly of the deodorization device 10. Preferably, the deodorizing element 30 is forced through the housing aperture 20 and past the lip 44 formed on the aperture sides 40, 42 to prevent removal of the element 30 back through the aperture 20. Most preferably, the deodorizing element 30 is slipped along the fingers 22 until it abuts the stops 54 at the finger distal ends 48.

Referring to FIG. 2, once deodorizing element 30 has been exposed to the malodorous vapors for a period of time, the spent deodorizing element 31 must be replaced in order for the deodorization device 10 to remain effective. The spent deodorizing element 30 is replaced by inserting a fresh deodorizing element 30 into the housing aperture 20, forcing the spent deodorizing element 31 out of the grasp of the fingers 22 and into the vent tube 12. The spent deodorizing element 31 is allowed to fall through the vent tube 12 and into the holding tank for disposal with the holding tank contents.

While there has been shown and described what are at present considered the preferred embodiment of the invention, it will be obvious to those skilled in the art that various changes and modifications can be made therein without departing from the scope of the invention defined by the appended claims.

What is claimed is:

1. A passive deodorization device suitable for use in a toilet enclosure having a vent tube for venting odors from a holding tank, said deodorization device comprising:

a housing having a wall fixable relative to an outer surface of the vent tube;

an aperture formed in said wall, and having a perimeter;

two or more fingers extending from said aperture perimeter defining an open ended passageway for receiving an element passed through said aperture, said fingers being extendable through an opening into the vent tube;

a retention member fixed to an outer surface of at least one of said fingers, and engageable with the vent tube for securing said wall to the vent tube when said fingers are extending through the opening in the vent tube; and a deodorizing element interposed between said fingers.

2. The deodorization device as in claim 1, wherein said deodorizing element is brick-shaped and said housing aperture is shaped to receive said brick-shaped deodorizing element.

3. A method for installing a deodorization device into a toilet having a vent tube for venting vapors from a holding tank, said method comprising the steps of:

forming a hole in a side of said vent tube;

inserting fingers extending from a deodorization device housing cavity into said vent tube hole; and engaging an interior surface of said vent tube with a retention member fixed to at least one of said fingers.

4. The method for installing a deodorization device as in claim 3, further comprising the step of inserting a deodorizing element into an aperture formed in said housing, and between said fingers.

* * * * *